US011484045B2

(12) United States Patent
Zeeck

(10) Patent No.: US 11,484,045 B2
(45) Date of Patent: *Nov. 1, 2022

(54) PROCESS FOR MANUFACTURING YEAST STRAINS HAVING INCREASED MANNAN OLIGOSACCHARIDES AND IMPROVED AMINO ACID PROFILES

(71) Applicant: AGVAULT PROPERTIES LLC, Gretna, NE (US)

(72) Inventor: James Russell Zeeck, Gretna, NE (US)

(73) Assignee: AGVAULT PROPERTIES, LLC, Gretna, NE (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/471,698

(22) Filed: Sep. 10, 2021

(65) Prior Publication Data

US 2022/0192228 A1 Jun. 23, 2022

Related U.S. Application Data

(63) Continuation of application No. 17/247,771, filed on Dec. 22, 2020, now Pat. No. 11,140,912.

(51) Int. Cl.
*A23K 10/38* (2016.01)
*A23L 33/145* (2016.01)
*A23K 20/163* (2016.01)
*A23K 10/16* (2016.01)
*C12N 1/16* (2006.01)

(52) U.S. Cl.
CPC .............. *A23K 10/38* (2016.05); *A23K 10/16* (2016.05); *A23K 20/163* (2016.05); *A23L 33/145* (2016.08); *C12N 1/16* (2013.01)

(58) Field of Classification Search
None
See application file for complete search history.

(56) References Cited

U.S. PATENT DOCUMENTS

| | | | |
|---|---|---|---|
| 7,820,418 B2 | 10/2010 | Karl et al. | |
| 9,861,700 B2 | 1/2018 | Andrade De Freitas et al. | |
| 10,519,475 B1 | 12/2019 | Walter et al. | |
| 10,582,723 B2 | 3/2020 | Cox et al. | |
| 2006/0263415 A1 | 11/2006 | Sedmak | |
| 2008/0108114 A1 | 5/2008 | Cox et al. | |
| 2015/0275158 A1* | 10/2015 | Heldt-Hansen | C12N 9/2428 426/16 |
| 2019/0127494 A1 | 5/2019 | Hruschka et al. | |

FOREIGN PATENT DOCUMENTS

| | | |
|---|---|---|
| BR | 102016028658 A2 | 7/2018 |
| CN | 104894186 A | 9/2015 |
| WO | 2019192873 A1 | 10/2019 |

OTHER PUBLICATIONS

Murthy, Ganti S., et al. "Starch hydrolysis modeling: application to fuel ethanol production." Bioprocess and biosystems engineering 34.7 (2011): 879-890. (Year: 2011).*
Bzducha-Wróbel et al., "Chemical composition of the cell wall of probiotic and brewer's yeast in response to cultivation medium with glycerol as a carbon source", Eur. Food Res. Technol., vol. 237, pp. 489-499, May 8, 2013.
Chaisuwan et al., "Microbial exopolysaccharides for immune enhancement: Fermentation, modifications and bioactivities", Food Bioscience, vol. 35, 17 pages, Mar. 6, 2020.
Feng et al., "Optimization of agitation, aeration, and temperature conditions for maximum p. mannanase production", Enzyme and Microbial Technology, vol. 32, pp. 282-289, 2003.
Gientka et al., "The exopolysaccharides biosynthesis by Candida yeast depends on carbon sources", Electronic Journal of Biotechnology, vol. 22, pp. 31-37, Mar. 11, 2016.
Hajhosseini et al., "Optimizing Growth Conditions of Kluyveromyces marxianus for Mannan Production as a Bioemulsifier", Applied Food Biotechnology, vol. 7(2), pp. 115-126, Jan. 26, 2020.
Kwak, Suryang, "Yeast Engineering for Pharmaceutical and Nutraceutical Purposes", Dissertation for the degree of Doctor of Philosophy in Food Science and Human Nutrition, University of Illinois at Urbana-Champaign, 147 pages, 2017.
Liu et al., "Statistical Optimization of Culture Media and Conditions for Production of Mannan by *Saccharomyces cerevisiae*", Biotechnology and Bioprocess Engineering, vol. 14, pp. 577-583, 2009.
Ejiofor et al., "Culture of *Saccharomyces cerevisiae* on hydrolyzed waste cassava starch for production of baking-quality yeast", Enzyme and Microbial Technology, vol. 18, pp. 519-525, 1996.
Akbari et al., "Optimization of baker's yeast drying in industrial continuous fluidized bed dryer", Food and Bioproducts Processing, vol. 90, pp. 52-57, 2012.
Pontoh et al., "Glucose syrup production from Indonesian palm and cassava starch", Food Research International, vol. 28, No. 4, pp. 379-385 1995.
Russell, Inge, "Understanding yeast fundamentals", The Alcohol Textbook, Ch. 9, pp. 85-119, 2003.
Nguyen et al., "Effect of Vacuum Pressure on Ethanol Fermentation", Journal of Applied Sciences, vol. 9(17), pp. 3020-3026, 2009.
Finn et al., "Near-infrared spectroscopic monitoring of biomass, glucose, ethanol and protein content in a high cell density baker's yeast fed-batch bioprocess", published online www.interscience.wiley.com, vol. 23, pp. 507-517, 2006.
Ejiofor et al., "Fed-batch production of baker's yeast using millet (*Pennisetum typhoides*) flour hydrolysate as the carbon source", Journal of Industrial Microbiology, vol. 16, pp. 102-109, 1996.

* cited by examiner

*Primary Examiner* — Robert J Yamasaki
(74) *Attorney, Agent, or Firm* — McKee, Voorhees & Sease, PLC

(57) ABSTRACT

The invention relates to production of a yeast strain with increased mannan oligosaccharides, amino acids, and complex carbohydrates. The invention further relates to the process to propagate and ferment such yeast. The invention further relates to methods of use of the yeast as a feed additive for animals and a food product for humans.

19 Claims, 3 Drawing Sheets

PROCESS FOR MANUFACTURING YEAST STRAINS HAVING INCREASED MANNAN OLIGOSACCHARIDES AND IMPROVED AMINO ACID PROFILES

CROSS-REFERENCE TO RELATED APPLICATION

This application is a continuation of U.S. Ser. No. 17/247,771, filed on Dec. 22, 2020, which is herein incorporated by reference in its entirety including without limitation, the specification, claims, and abstract, as well as any figures, tables, or examples thereof.

FIELD OF THE INVENTION

The invention relates to the industrial scale production of unique yeast strains with increased complex carbohydrates, specifically mannan oligosaccharides, and improved amino acid profiles as compared to prior art yeast. Further, the invention relates to a process designed to propagate, ferment, and produce new and unique yeast strains. Additionally, the invention relates to a method of use of the new and unique yeast strains as an animal feed additive.

BACKGROUND OF THE INVENTION

Traditional and established yeast propagation and production processes manufacture yeast almost entirely for its ability to act as a leavener or to produce ethanol and alcohol. The invention produces yeast to be used for its innate probiotic and nutritional value instead of current art yeast that is made to enable a process or functions as a catalyst for baking and fermentation.

Current art commercial yeast manufacturing utilizes simple sugars such as glucose and sucrose as the energy source to propagate and manufacture yeast. Such simple sugars are added to a growth medium comprised of water and trace nutrients into which seed yeast is propagated in batches and then transferred to large fermentation tanks where yeast production is completed. This traditional and standard yeast is then dried and mostly used for leavening, alcohol or ethanal fermentation, and the like.

Yeast is also used as a part of contemporary animal nutrition by using yeast in the animal feed industry as a ration additive. This ration-additive yeast is produced using current art processes but with the addition of expensive protein enrichment supplements such as methionine, lysine, and/or tryptophane. Synthetic methionine and lysine are commercially mass-produced; however, the cost of these amino acids is prohibitive when compared with the more common natural sources of amino acids from other feed proteins such as soy meal, alfalfa, fish meal, and similar sources. Furthermore, these amino acids often need to be added in concentrated forms so that a protein deficiency may be remedied without causing an imbalance among other amino acids in the ration blend which could result in negative performance issues in the animal as well as negative economic impacts to the producer. Naturally produced amino acids are hydrolyzed by the animal's digestive tract and absorbed in a gradual, steady manner. Essential amino acids naturally produced are digested and absorbed more efficiently than amino acids ingested in a concentrated free state such as synthetic amino acid feed additives.

Yeast cell nutrient metabolism can be enhanced by varying its osmotic properties. The osmotic properties of a yeast cell are primarily controlled by selective permeability of the cell wall as determined by conditions of the medium in which the yeast is reproducing and being grown. By controlling and enhancing its osmotic properties, yeast cell nutrient metabolization can be improved by increasing the percentage and distribution throughout the cell of complex carbohydrates. Precise management of nutrient metabolism can improve the yeast cell's amino acid profile and output including the level of mannan oligosaccharides ("MOS") and other beneficial complex carbohydrates while at the same time reducing the production of alcohol and organic acids such as lactic acid which can inhibit yeast performance. MOS is one of the complex carbohydrates in the *Saccharomyces Cerevisiae* yeast cell wall and is known for its ability to bind its threadlike fimbriae on pathogenic bacteria, preventing such bacteria from attaching to the animal gut wall, thus inhibiting bacteria colonization and multiplication. MOS ingestion has been demonstrated to be a viable solution for antibiotic fee diets in multiple animal species as well as furnishing effective support for digestion and immunity in dairy cattle especially during calf season.

Like MOS, glycoproteins contain oligosaccharides and are involved in diverse biological functions such as antigenicity, solubility, cell adhesion, cell recognition, and immune function. Antigenicity is critical to developing the immune system primarily through the development of T-cells and antibodies. MOS contained in the yeast cell is a source of oligosaccharides.

Accordingly, it is an objective of the invention to provide a scalable manufacturing process to produce yeast with increased levels of MOS and other complex carbohydrates and amino acids. A further objective of the invention is to produce yeast strains with increased levels of MOS and other complex carbohydrates and increased levels of amino acids. Another objective of the invention is to provide yeast strains to be used as a feed additive to improve feeding economics, supplant antibiotics and other medications, and improve animal health and growth performance.

Growing threats of antibiotic resistance and negative public perception of antibiotic use in animal agriculture have led to rapid growth of the livestock nutraceutical industry to maintain and bolster animal health and performance. *Saccharomyces* yeast species have been shown to be an effective probiotic in this regard, and are well-suited to industrial-scale production as demonstrated by the brewing and biofuel industries. However, the attributes of yeast cultivated or produced for ethanol or biofuels production differ from the yeast components highlighted as beneficial in livestock diets. Of particular focus, are the yield and profile of amino acids, cell wall glycoprotein yield, and simple carbohydrate content from cultured yeast. This process seeks to identify candidate probiotic yeast strains and optimize their cultivation via rapid, high-throughput assays for the nutritional components of interest.

Other objects, advantages, and features of the present invention will become apparent from the following specification taken in conjunction with the accompanying figures.

BRIEF SUMMARY OF THE INVENTION

Disclosed herein is a process for producing a yeast with increased levels of amino acids and complex carbohydrates including mannan oligosaccharides, the process comprising providing a seed yeast, a sugar source, air, and nutrients to at least one propagator for propagation creating a propagation medium therein, then providing at least a portion of the propagation medium, a sugar source, air and nutrients to at least one fermenter for fermentation creating a fermentation medium therein, thereafter separating a yeast cream from the fermentation medium, and then drying the yeast cream to produce a yeast product.

In an aspect the sugar source comprises DP1, DP2, DP3, and DP4 sugars. In an aspect the sugar source comprises from about 70 wt-% to about 80 wt-% DP1 sugar, from about 5 wt-% to about 15 wt-% DP2 sugar, from about 5 wt-% to about 15 wt-% DP3 sugar, and from about 1 wt-% to about 10 wt-% DP 4 sugar. In another aspect the sugar source comprises glucose, maltose, maltotriose, and dextrin. In another aspect, the nutrients comprise one or more of a nitrogen source, a phosphorus source, minerals, vitamins, and pH control.

In various embodiments, the propagator of the process disclosed herein comprises a stainless steel tank, is from about 10% to about 30% of the capacity of the fermenter, further comprises a cooling system wherein the temperature inside the propagator is maintained between about 82° F. and about 90° F., further comprises at least one agitator and at least two baffles, and comprises an air vent wherein pressure in the propagator is from about 5 psi to about 15 psi. In an aspect, propagation proceeds until the yeast in the propagation medium comprises about 40% to about 75% budding and from about 60% to 90% viability and the propagator reaches a capacity of about 80% to about 100%.

In various embodiments, the fermenter of the process disclosed herein comprises a stainless steel tank, comprises a volume of about 50,000 to about 200,000 gallons, further comprises a cooling system wherein the temperature is maintained between about 86° F. and about 90° F., further comprises at least one agitator and at least two baffles, and comprises an air vent wherein pressure in the fermenter is from about 5 psi to about 10 psi. In an aspect, the sugar source is added throughout fermentation process at a rate of about 1 gallon per minute to about 80 gallons per minute. In an aspect, the fermenter maintains an oxygen to $CO_2$ ratio of from about 2 to about 6 and a pH of between about 4 and about 6. In another aspect, oxygen saturation levels in the fermentation medium are from about 50% to about 95% and wherein dissolved oxygen levels are from about 8 ppm to about 25 ppm.

In an aspect, the processes disclosed herein are monitored with high-performance liquid chromatography, near-infrared analysis, grid smear examination, and growth curves.

The process and methods disclosed herein may comprise one or many propagators and may comprise one or many fermenters. The propagators and fermenters of the process and methods described herein may be configured to adjust sugar source, air, nutrients, and pressure to maintain yeast viability and yeast budding levels.

Disclosed herein is a process for the production of yeast strains with increased complex carbohydrates comprising MOS and increased amino acids. Specifically, propagation and fermentation at an industrial scale of such yeast strains.

Disclosed herein is a process for controlling osmotic pressure around a yeast cell wall comprising providing a yeast propagation medium, a sugar source, air and nutrients to at least one fermenter for fermentation creating a fermentation medium therein, wherein the fermenter comprises at least one agitator and at least two baffles, wherein the fermentation is under aerobic conditions, and wherein an oxygen to $CO_2$ ratio in the fermenter is from about 2 to about 6.

Disclosed here is a yeast product that comprises at least about 2 wt-% more complex carbohydrates, at least about 0.5 wt-% more amino acids, and/or at least about 0.1 wt-% more mannan oligosaccharides than prior art yeast products.

Disclosed herein is an animal feed and a human food additive comprising the yeast product of the processes and methods disclosed herein.

While multiple embodiments are disclosed, still other embodiments of the present invention will become apparent to those skilled in the art from the following detailed description, which shows and describes illustrative embodiments of the invention. Accordingly, the figures and detailed description are to be regarded as illustrative in nature and not restrictive.

Figure 1:
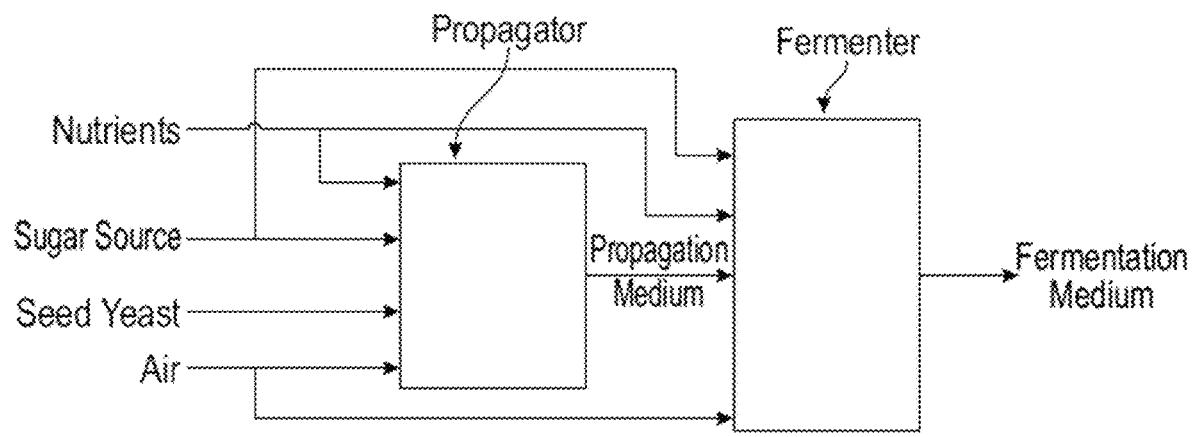
FIG. 1 is a block diagram of an embodiment of the process according to the present invention.

Various embodiments of the present invention will be described in detail with reference to the figures, wherein like reference numerals represent like parts throughout the views. Reference to various embodiments does not limit the scope of the invention. Figures represented herein are not limitations to the various embodiments according to the invention and are presented for exemplary illustration of the invention.

DETAILED DESCRIPTION OF THE INVENTION

The present disclosure relates to a process for the production of yeast strains with increased complex carbohydrates, including MOS, and increased amino acids. Specifically, the process comprises propagation and fermentation of such yeast strains at an industrial scale, such that the yeast strains have increased MOS. For example, the yeast product produced by the processes, systems, and methods described herein exceed the prior art yeast strains in amount of all complex carbohydrates by at least about 2 wt-%, preferably by at least about 5 wt-%, more preferably by at least about 8 wt-%. Amino acids in yeast strains produced by the processes, systems, and methods described herein exceed the prior art yeast strains by about 0.5 wt-% and preferably by at least about 2 wt-%. Further, the present disclosure describes methods of use of the yeast product as an animal feed additive and/or a human feed additive and/or probiotic.

The embodiments of this invention are not limited to particular systems and/or methods, which can vary and are understood by skilled artisans. It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form.

Numeric ranges recited within the specification are inclusive of the numbers defining the range and include each number within the defined range. Throughout this invention, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges, fractions, and individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6, and decimals and fractions, for example, 1.2, 3.8, 1½, and 4%. This applies regardless of the breadth of the range. Yeast production involves the management of a living biological system which is subject to variances and outcomes that can be outside of expected results or calculations.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will be used in accordance with the definitions set out below.

The term "about," as used herein, refers to variation in the numerical quantity that can occur, for example, through typical measuring techniques and equipment, with respect to any quantifiable variable, including, but not limited to, mass, volume, time, and the like. Further, given solid and liquid handling procedures used in the real world, there is certain inadvertent error and variation that is likely through differences in the manufacture, source, or purity of the ingredients used to make the compositions or carry out the methods and the like. Whether or not modified by the term "about," the claims include equivalents to the quantities.

The methods and systems of the present invention may comprise, consist essentially of, or consist of the components and ingredients of the present invention as well as other ingredients described herein. As used herein, "consisting essentially of" means that the methods, systems, apparatuses and compositions may include additional steps, components or ingredients, but only if the additional steps, components or ingredients do not materially alter the basic and novel characteristics of the claimed methods, systems, apparatuses, and compositions.

The term "weight percent," "wt. %," "wt-%," "percent by weight," "% by weight," and variations thereof, as used herein, refer to the concentration of a substance as the weight of that substance divided by the total weight of the composition and multiplied by 100.

As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged, constructed, adapted, manufactured, and the like.

Process for Yeast Production

Figure 2:
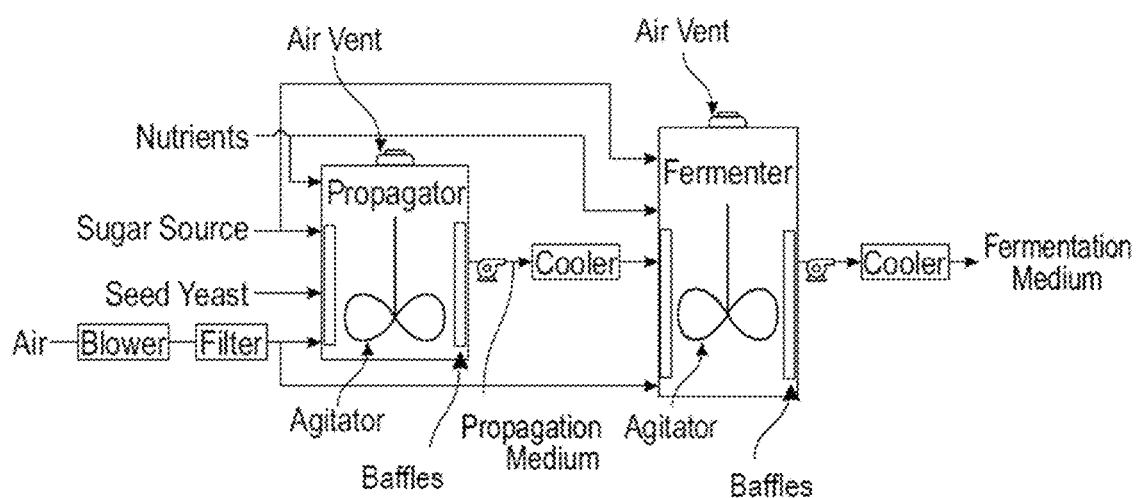
FIG. 2 is a block diagram of an embodiment of the invention comprising one propagator and one fermenter.

A block diagram of an exemplary embodiment of the yeast production process according to the invention comprising one propagator and one fermenter is illustrated in FIG. 1 and FIG. 2. In this embodiment, nutrients, a sugar source, seed yeast, and air are inputted into the propagator wherein yeast propagation according to the invention occurs. The propagation medium is then transferred into a fermenter, along with nutrients, a sugar source, and air, wherein yeast fermentation occurs according to the invention. As illustrated in FIG. 2 the propagator and fermenter each comprise an air vent for pressure control and an agitator and tank baffles for efficient mixing of the medium contained therein. Further, as illustrated in FIG. 2, the propagation medium may be cooled prior to transfer of the medium to the fermenter, and the fermentation medium may be cooled after fermentation. The fermentation medium is then sent for further processing such as concentration and separation of the yeast solids, drying, grinding, storage, packaging, and the like.

As used herein, "yeast" refers to the *Saccharomyces cerevisiae* species.

As used herein, seed yeast refers to a pure yeast strain used for propagation and/or fermentation. In an aspect, seed yeast is created and grown in sterile conditions in a laboratory environment wherein a pure yeast culture is combined with sterile fermentable DP4, DP3, DP2, and/or DP1 sugars, other nutrients, and warm water to form a sterile seed yeast.

As used herein, "medium" refers to the contents of the propagator and/or fermenter and comprises yeast, sugar source, air, $CO_2$, and/or additional nutrients, and/or combinations thereof. The medium is temperature and pH controlled at all times during the process.

Figure 3:
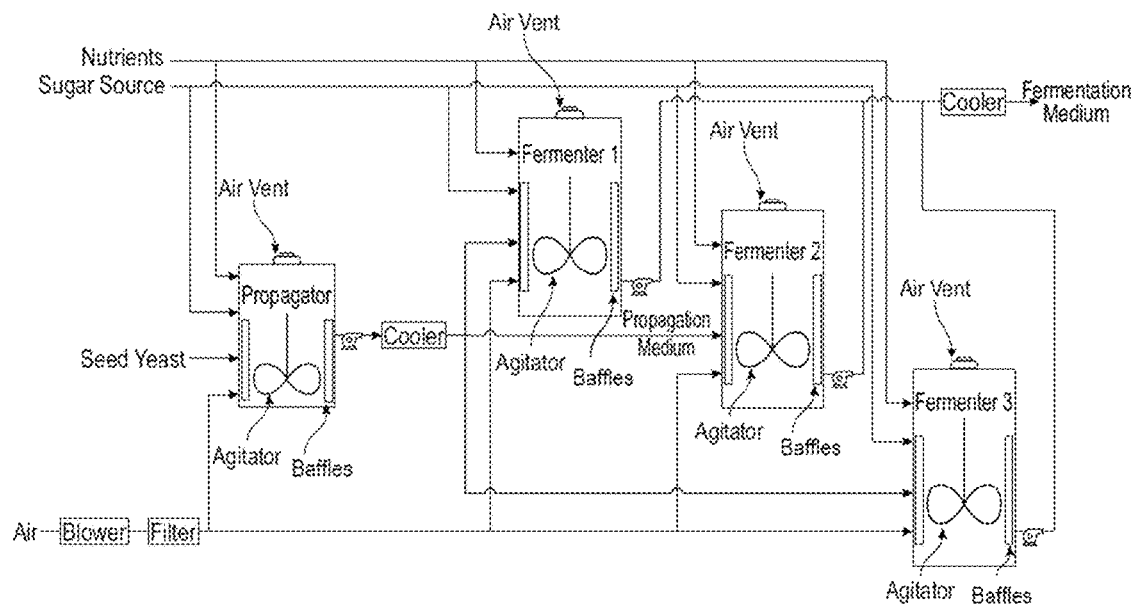
FIG. 3 is a block diagram of an embodiment of the invention comprising one propagator and three fermenters.

In a preferred embodiment, as exemplified by FIG. 3, a seed yeast is provided to at least one yeast propagator wherein the yeast strain feed is propagated according to the invention with the addition of air, nutrients, and a sugar source to the propagator. At least a portion of the propagation medium is then cooled and transferred to three fermenters wherein the yeast is produced via fermentation according to the invention, with the addition of a sugar source, nutrients, and air to each fermenter. The propagator and fermenters in this embodiment each comprise an air vent at the top of each for pressure control and each further comprise an agitator and tank baffles for efficient mixing of the medium contained therein. After fermentation, the yeast medium is sent for further processing, for example concentration and separation of the yeast solids, drying, grinding, packaging, storage, and the like.

Propagators

As used herein, a propagator is a vessel in which yeast is grown and multiplied prior to fermentation. In an aspect, a propagator is a small fermenter. This disclosure is meant for the propagator to include all descriptions of a fermenter and vice versa, except for size. In an embodiment, the propagator may be from about 10% to about 30% of the capacity of the fermenter. In an embodiment, the propagator comprises a vessel that is made of low pH tolerant material. In a preferred embodiment, the propagator comprises a stainless steel tank. In one embodiment, the volume of the propagator is from about 5,000 gallons to about 50,000 gallons.

Air is introduced into the propagation medium through a distribution manifold in the propagator. In an embodiment, the air is compressed. In another embodiment, the air is filtered such that the air is free of contaminants such as spores, pollen, and/or dirt particles and the like. In another embodiment, the air is both compressed and filtered. In an aspect, air is metered into the propagation tank through manifolds with small holes to uniformly disperse the air throughout the propagation medium to obtain oxygen saturation and $CO_2$ disbursement. The air hole size depends on tank volume and dimensions. In an embodiment, baffles on the interior of the propagator comprise the air holes. In an aspect, air flow rate is adjusted based on the oxygen saturation in the medium.

In an aspect, oxygen concentration levels are monitored and maintained at saturation levels from about 50% to about 95%. In a preferred embodiment, oxygen saturation level is maintained at from about 72% to about 80%. In an aspect, the air flow rate is adjusted to maintain the oxygen levels in the propagator.

The propagator comprises a cooling system to remove heat generated and to control the temperature of the medium. The cooling system may be any such cooling system or chiller as known in the art and may be internal or external relative to the propagator. In an embodiment, the cooling system comprises cooling coils and/or rods imbedded into the interior of the propagator, and/or combinations thereof. In an embodiment, external cooling could include plate and frame coolers, spiral coolers, or tube and shell coolers. In an embodiment, the cooling system maintains the temperature between about 82° F. and about 92° F.

The propagators of the invention may further comprise at least one multi-blade, multi-level, variable pitch, variable speed agitator and baffles for adequate mixing and dispersion to augment and maximize yeast propagation. The agitator aids in both oxygen and $CO_2$ dispersion in the propagation medium while maintaining and controlling propagation pressure inside the vessel which assists in controlling osmotic pressure on the yeast cells. The agitator may be any such agitator as known in the art and comprise, for example, a mechanical agitator, a static agitator, a rotating tank, a mixer, a paddle mixer, an impeller, a propeller, vibration, oscillation, and the like, and/or combinations thereof. In an embodiment, the agitator comprises at least one impeller and at least one paddle mixer. In a preferred embodiment, the propagation vessel further comprises two or more baffles as a part of the agitation system. In an aspect, baffle placement and size are determined for efficient circulation and mixing of the propagation medium. In an embodiment, the baffles are placed equidistantly around the perimeter of the propagator. The baffles may comprise any height and extend into the interior of the propagator any distance sufficient to maintain efficient mixing. The pressure in the propagator is maintained from about 5 psi to about 15 psi. In an embodiment, the propagator comprises an air vent to vent a portion of the air and $CO_2$ inside the propagator when the pressure is too high. In an aspect, the air vent is near the top or at the top of the propagator. In an embodiment, the air vent further comprises an air purifier as known in the art. In an embodiment, the air purifier comprises an air scrubber, a thermal oxidizer, or a $CO_2$ production plant.

The Propagation Process

According to the process of the invention, at least one propagator is initially filled to a capacity level of about 1% to about 10% with the sugar source. Seed yeast is added to the propagator. Air, nitrogen, minerals, and vitamins are introduced into the propagator, and mixing commences, all in any order. The sugar source continues to be added as the yeast mass grows to maintain about 6% to about 12% yeast solids in the medium and until the propagation tank reaches a capacity of about 80% to about 100%.

Nutrients and additional sugar source are metered into the propagation medium as needed for yeast growth. The flow rate for nutrients into the propagator is from about 10 ml/l to 500 ml/l. The flow rate may vary between nutrients. In an aspect, the flow rate of the sugar source into the propagator will depend upon the rate of propagation and budding. In an aspect, the flow rate of nutrients into the propagator will depend upon the rate of propagation and budding. Excess $CO_2$ and excess air are discharged from the top of the propagator when pressure exceeds a maximum level. In an embodiment, excess $CO_2$ and excess air are discharged by an ambient or controlled source air vent to a vent scrubber and/or combinations thereof.

As used herein, "nutrients" are added to the medium for yeast growth and to establish the yeast metabolization pathway to increase complex carbohydrates in the yeast, including MOS, and increase amino acid profiles as compared to prior art yeast. Nutrients metered into the propagation medium may comprise a nitrogen source, a phosphorus source, minerals, vitamins, and/or a pH control and/or combinations thereof. In an embodiment, the nitrogen source comprises one or more of anhydrous ammonia, liquid urea, bagged urea, ammonium sulfate, and/or combinations thereof. In an embodiment, the phosphorus source comprises phosphoric acid, potassium dihydrogen phosphate, and/or natural occurring phosphate from the sugar source, and/or combinations thereof. In an embodiment, added minerals comprise magnesium, and/or zinc, and/or combinations thereof. In an embodiment, the vitamins comprise one or more of biotin, thiamin, folic acid, inositol, niacin, pantothenate, pyridoxine, riboflavin, some of which may be found in the sugar source, and/or combinations thereof. In an embodiment, the pH control comprises one or more of phosphoric acid, anhydrous ammonia, sulfuric acid, naturally occurring organic acids from the sugar source, and/or combinations thereof.

The propagation process proceeds until such time as the yeast in the propagation medium comprises about 40% to about 75% budding and from about 60% to about 90% viability. As used herein, "budding" refers to the asexual reproduction by division, and percent budding refers to the portion of yeast that is asexually reproducing. As used herein, "viability" refers to the amount of living yeast cells in the medium. In an aspect, viability may be expressed via a growth curve. In an embodiment, budding and viability are assessed visually. In an embodiment, budding and viability are measured periodically. In an embodiment, budding and viability are measured approximately every 2-4 hours. In an embodiment, the propagation process proceeds until the propagator is at least about 80% full. In an embodiment, the propagation process extends from about 5 hours to about 18 hours. A portion of the propagation medium is then transferred into at least one fermenter. In an embodiment, the entire propagation medium is transferred into at least one fermenter. In an embodiment, the propagator is cleaned and sanitized after each propagation process before being used for the next propagation process.

In an embodiment, the propagation medium is cooled to maintain a temperature from about 86° F. to about 90° F. before the medium is transferred into at least one fermenter.

According to the invention, the process includes at least one propagator and can include many more. In a system with more than one propagator, each propagator may be identical, or each may differ according to the invention. The propagators may transfer the propagation medium contained therein to one or more fermenters. Each propagator may transfer the medium contained therein to a single fermenter, or more than one propagator may transfer the medium contained therein to a single fermenter. In an embodiment, the process can include multiple propagators and multiple fermenters.

Fermenters

As used herein, a fermenter is a vessel in which yeast fermentation and production occurs. In an embodiment, the fermenter comprises low pH tolerant material. In an embodiment, the fermenter comprises a stainless steel tank. In an embodiment, the fermenter of the invention has a diameter to accommodate between 24 and 30 hours of retention time depending on the desired production capacity. In an embodiment, the volume of a fermenter is from about 50,000 gallons to about 200,000 gallons.

The fermenter of the invention comprises an air distribution system for the distribution of air into the fermentation medium to disperse the air throughout the fermentation medium to obtain oxygen saturation and $CO_2$ disbursement. In an embodiment, the air distribution system comprises a manifold. In an embodiment, air distribution comes from the tank bottom near the baffles through the recycle line from an external cooling system. In an embodiment, the air is compressed. In another embodiment, the air is filtered such that the air is free of contaminants such as spores, pollen, dirt particles, and the like. In an aspect, the air may be filtered by any means known in the art. In another embodiment, the air is both compressed and filtered. In another embodiment, the air is neither compressed nor filtered. In an embodiment, compressed and filtered ambient air is metered into the fermenter through manifolds with small holes to uniformly disperse the air throughout the fermentation medium. In a preferred embodiment, baffles on the interior of the fermenter comprise the air holes.

In an embodiment, the fermenter further comprises a cooling system to remove the heat generated by fermentation and to control the temperature of the fermentation medium. The cooling system may be any such cooling system or chiller as known in the art and may be internal or external to the fermenter. In an embodiment, the cooling system comprises an external heat exchanger. In an embodiment, the cooling system comprises an external cooling loop that comprises a cooling tower or chiller or combination thereof. This is accomplished by using cooled water circulated in cooling coils located inside the propagators and/or fermenters or by external heat exchangers that use a recirculating stream from the propagators and/or fermenters to maintain the desired temperature. External cooling can include plate and frame coolers, spiral coolers, or tube and shell or coils or rods placed in the propagator or fermenter interior and/or a combination thereof. The fermentation process is maintained at a temperature between about 86° F. and about 90° F.

The fermenter of the invention may comprise at least one agitator and may further comprise baffles for efficient mixing. In an embodiment, the agitator may be a multi-blade, multi-level, variable speed agitator. In a preferred embodiment, the fermenter comprises at least one agitator and two or more baffles. In a preferred embodiment, the fermenter comprises four or more baffles. Baffle placement and size is determined for efficient circulation and mixing of the fermentation medium. In an embodiment, the baffles are placed equidistantly around the perimeter of the fermenter. The baffles may comprise any height and extend into the interior of the fermenter any distance sufficient to maintain efficient mixing. The design of the agitation system and baffles are such that the fermentation medium is kept in suspension and in uniform and steady contact with oxygen, the sugar source, and/or other nutrients. Moreover, the agitator pitch and baffle design of the invention allows for the quick release of $CO_2$ and further allows for efficient air distribution and oxygen saturation of the fermentation medium. This disclosure is meant to include any such agitator as known in the art. Embodiments include paddle agitators, anchor type agitators, propeller agitators, turbine agitators, helical agitators, screw type agitators, gate agitators, oscillation agitators, vibration agitators, and combinations thereof and the like. In an embodiment, the agitator is center-mounted. In an embodiment the agitator comprises at least one impeller and at least one paddle mixer The pressure in the fermenter is maintained at from about 5 psi to 10 psi. In an embodiment, the fermenter comprises an air vent to vent a portion of the air and/or $CO_2$ inside the propagator when the pressure is too high. In an aspect, the air vent is near the top, or at the top, of the fermenter. In an embodiment, the air vent further comprises an air purifier as known in the art. In an embodiment, the air purifier comprises an air scrubber The Fermentation Process According to the process of the invention, at least a portion of the propagation medium of at least one propagator is added into at least one fermenter. Air is added into the fermenter and agitation begins. Agitation may begin before or after air is added into the fermenter and may begin before or after the medium from the propagator is added into the fermenter. In an aspect, once the medium is adequately mixed and the yeast growth continues, additional sugar source, and/or nutrients are metered into the medium. In an embodiment, the metering rate is such that the additional sugar source closely matches the consumption level of the sugar source by the yeast colony, therefore exposing the yeast colony cells to the higher DP sugars such that the yeast cells absorb such sugars as well as minimizing the buildup of excess sugar in the yeast fermentation medium. The sugar source flow rate into the fermenter is from about 1 gallon per minute ("GPM") to about 80 GPM based on the yeast growth rate and associated sugar source consumption. In an embodiment, high-performance liquid chromatography ("HPLC") is used to monitor the sugar profile in the fermentation and propagation mediums. A representative HPLC chromatogram output table is shown in Table 1. HPLC will monitor DP1-4 sugar profiles in the medium, confirm near infrared image monitoring (explained below) results of the medium, and measure fermentation progress. The flow rate of the additional sugar source is adjusted based on the HPLC monitoring results of the medium's sugar profile.

TABLE 1

Exemplary HPLC analysis output of fermentation liquor of a 60-hour mash from a dry corn.

| Component | Retention time (min) | Amount* (g l$^{-1}$) |
|---|---|---|
| Dextrin (e.g. Maltotetraose) | 7.9 | 14.4 |
| Maltotriose | 8.6 | 0.9 |
| Maltose | 9.6 | 3.0 |
| Citric acid | 10.8 | 0.7 |
| Glucose | 11.2 | 3.3 |
| Fructose | 12.2 | 0.4 |
| Succinic acid | 15.1 | 0.4 |
| Lactic acid | 16.2 | 4.6 |
| Glycerol | 16.8 | 6.8 |

TABLE 1-continued

Exemplary HPLC analysis output of fermentation liquor of a 60-hour mash from a dry corn.

| Component | Retention time (min) | Amount* (g l$^{-1}$) |
| --- | --- | --- |
| Acetic acid | 18.9 | 0.6 |
| Methanol | 23.1 | 2.2 |
| Ethanol | 25.6 | 12.0 |

*Units are in g l$^{-1}$ except for ethanol, which is in vol.%.

Figure 4:
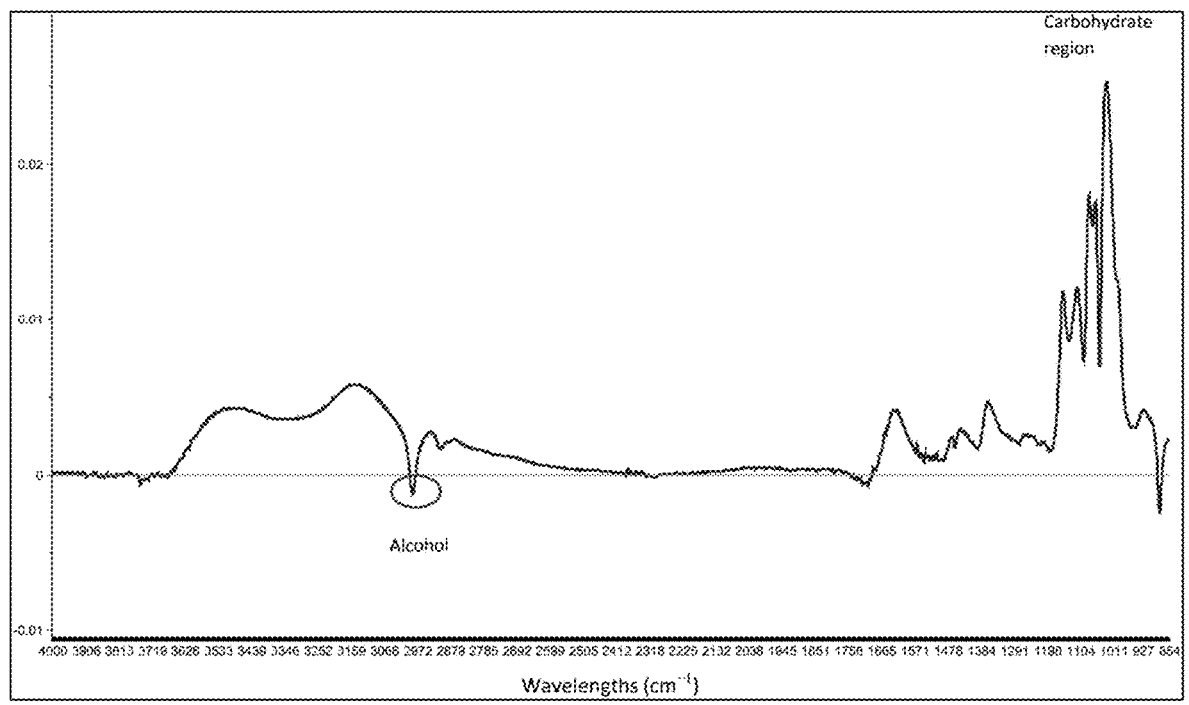
FIG. 4 is a representative near infrared image monitoring propagation rate and yeast cell mass for a fermentation process according to the invention.

Applicable fermentation nutrients are as described for the propagation process. The flow rate for nutrients into the fermenter is from about 10 ml/l to 500 ml/l. The flow rate may vary depending on the nutrient. The flow rate of nutrients into the fermenter will depend upon the rate of fermentation and budding which in an embodiment is monitored with HPLC and/or near infrared ("NIR") scanning of samples. A representative NIR sugar profile output image is shown in FIG. 4. The horizontal axis indicates wavelength, sometimes expressed in terms of a wavenumber. The vertical axis reflects transmittance, and the scale may be altered for a specific compound and/or composition being investigated. NIR monitors: i) complex carbohydrate and protein production in the yeast; ii) oxygen and nitrogen saturation in the medium; and/or iii) yeast cell mass. NIR monitoring results can ensure maximum MOS and amino acid output during the fermentation stage.

In addition to HPLC and NIR monitoring, in an embodiment, yeast cell viability and budding count (cellular phenomena such as regulation of the cell cycle, aging, and cell death) will be monitored by microscopic examination of grid slide smears and cell mass of the growth curve using a spectrophotometer. In an embodiment, with these three monitoring systems (HPLC, NIR, grid smear examination), fermentation profiles, cell health, harvest timing, and/or output levels can be optimized.

In an embodiment, $CO_2$ and excess air are discharged from a top portion of the fermenter to maintain a proper oxygen:$CO_2$ ratio and proper tank pressure. In an embodiment, $CO_2$ and excess air are discharged by an ambient air vent, a vent scrubber, and/or combinations thereof. The oxygen:$CO_2$ ratio in the fermenter is maintained between from about 2 to about 6. In an aspect, the pressure inside the fermenter may be maintained from about 5 psi to about 10 psi. In an aspect, temperature inside the fermenter is maintained between about 86° F. and about 90° F. In an aspect, pH level in the fermenter is maintained between about 4.0 and about 6.0. In an embodiment, oxygen, nitrogen, and $CO_2$ levels in the fermenter are monitored to maintain aerobic conditions for maximum yeast growth and to retard the production of ethanol, glycerol organic acids, and other byproducts. In an aspect, oxygen concentration levels are monitored and maintained at dissolved levels from about 8 ppm to about 25 ppm. In a preferred embodiment, oxygen saturation level is maintained at from about 85% to about 95% in the first stage of the yeast growth curve which equates to about 18 ppm dissolved oxygen in the medium. In an aspect, as the growth curve extends past about 12 hours, the amount of dissolved oxygen falls to as low as about 8 ppm. In an aspect, air flow rate is adjusted to maintain the oxygen levels in the fermenter. The flow rate or addition of nitrogen into the fermenter is based on the need to maintain from about 5 gallons/l to about 8 gallons/l. NIR scanning of samples will be used to measure nitrogen levels in the fermenter. As described herein, oxygen levels are controlled via air flow rate into the fermenter.

In an aspect, the percent yeast viability is maintained at from about 82% to about 94%. In another aspect, the budding levels within the yeast colony are maintained at about 70% to about 80%. In an aspect, the fermenter is configured to adjust the sugar source, oxygen, nitrogen, and/or $CO_2$ levels to maintain the budding and viability levels. In an aspect, nutrients and pH are also monitored and adjusted to maintain budding and viability levels.

Figure 5:
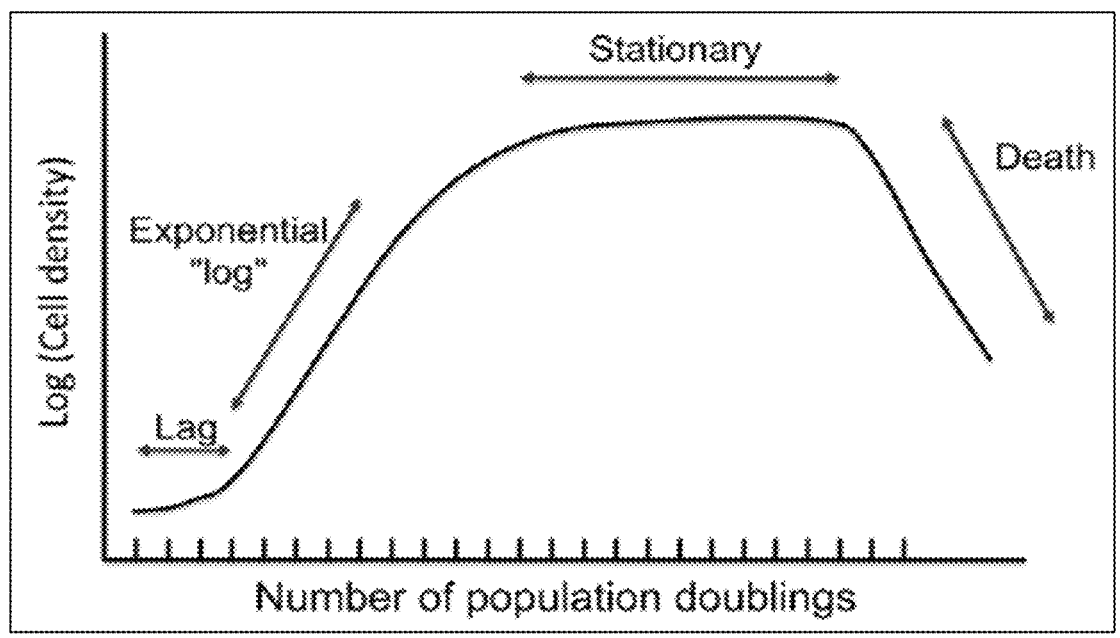
FIG. 5 is an exemplary growth curve for a fermentation process according to the invention.

In an embodiment, the fermentation process proceeds until such time as the fermentation growth curve plateaus, also known as the stationary period. As used herein, "growth curve" refers to the measure of the amount of total biomass over time. An example of a growth curve is shown in FIG. 5. During the lag period, most byproducts are extracted in current art yeast fermentation such as ethanol and alcohol. In an embodiment, the methods and processes described herein will harvest yeast colony at the peak growth stage of the production just as the exponential "log" growth period ends and the stationary growth period begins (as shown in FIG. 5). The exponential growth of yeast can be described by the equation in Formula (I) wherein N represents the number of cells at any time (t), and No represents the number of cells at the beginning of the interval being analyzed. The growth constant k is sometimes conveniently considered in terms of the doubling time of the culture. As rendered in FIG. 5, k=ln 2/T, wherein T is the doubling time of the culture. During this yeast growth curve transition period from exponential "log" to stationary, complex carbohydrates are being metabolized and the highest level of MOS and amino acids are contained in the yeast cell mass.

$$N = N_0 e^{kt} \qquad (I)$$

In an embodiment, the conditions of the propagation and/or fermentation process as described herein control the osmotic pressure around the yeast cell wall. As described herein, "osmotic pressure" refers to the force that develops between two solutes of differing concentration separated by a semi-permeable membrane, here the yeast cell wall. Increasing osmotic pressure too high may result in a decrease in yeast cell viability, growth, fermentation/propagation performance, and yeast cell volume. In an aspect, when osmotic pressure is too high, the yeast cell may comprise a wrinkled and/or less rounded shape. In an embodiment, osmotic pressure is controlled in the propagation and/or fermentation processes described herein allowing increased nutrient absorption of the yeast cell, increased viability of the yeast cell, and/or reduced fermentation and/or propagation time, and/or combinations thereof. In an embodiment, the volume of the yeast cell produced by the process and methods described herein is increased. In an embodiment, osmotic pressure is managed and/or maintained by inputs to the system comprising agitation conditions, the presence and/or dimensions of any baffles, air distribution within the medium, and/or conditions of the medium, and/or combinations thereof.

In an embodiment, aerobic conditions for fermentation and/or propagation is maintained in the fermenters and propagators. In an aspect, the output of aerobic fermentation and aerobic propagation processes comprise $CO_2$ and water. In an aspect, aerobic conditions minimize and/or reduce alcohol levels, organic acids such as lactic acid, and $CO_2$ in the fermentation and/or propagation mediums. In an aspect, elevated alcohol and organic acid levels can inhibit propagation and/or fermentation according to the invention.

In an embodiment, fermentation proceeds until the fermenter is about 75% to about 90% full. In an embodiment, fermentation takes about 6 to about 30 hours. In a preferred embodiment, fermentation takes from about 20 to about 30 hours. In an aspect, at least a portion of the fermentation medium is then emptied from the fermenter. In an embodiment, the fermentation medium is sent for further processing. In an embodiment, the fermentation medium is transferred into a concentration centrifuge wherein the yeast cream is separated from the fermentation medium. In an embodiment, the empty fermenter is thoroughly cleaned and sanitized after each fermentation process before being used for the next fermentation process.

According to the invention, the process includes at least one fermenter, and can include many more. In a system with more than one fermenter, each fermenter may be identical, or each may differ according to the invention.

Yeast Concentration, Drying, Further Processing

In an embodiment, the fermentation medium after fermentation is complete comprises from about 6 wt-% to about 10 wt-% total solids and from about 4 wt-% to about 8 wt-% yeast solids. In an embodiment, the fermentation medium is transferred to a system wherein yeast cream is concentrated and separated from the medium by any system or process or method as known in the art. In an embodiment, the yeast cream concentration and separation occur in a centrifuge wherein the yeast cream is separated from a version of the medium. In an embodiment, the centrifuge is a nozzle bowl centrifuge. In an aspect, the yeast cream after concentration and separation comprises from about 18% to about 22% yeast solids.

In an embodiment, the collected yeast cream is sent for further processing such as drying, pasteurization, grinding, storage, packaging, and the like. In an embodiment, the yeast cream is transferred to at least one drum dryer wherein steam heated rotary drums remove the moisture from the yeast cream. In this embodiment, the yeast cream is fed between two rotating drums and evenly spread over the surface of the drums wherein the drums are heated internally with steam, heated air spray, belt, or ultrasonic (microwave) dryers. Water evaporated from the dried yeast cream is captured and exhausted. In an aspect, the dried yeast comprises from about 5% to about 10% moisture. The dried yeast may then be sent on for further processing, such as grinding, or into storage and packaging. In an embodiment, a pneumatic conveying system conveys the dried yeast into a storage containment system for storage and packaging wherein the pneumatic conveying system further removes moisture from the dried yeast and cools the yeast through pneumatic cooling. Notably, the process described herein does not require low temperature cooling like in yeast production for baker's yeast. The yeast strain described herein does not require low temperature processing to maintain the yeast viability because it is used as a nutrient feed additive.

Sugar Source

Any raw material containing sugar or any starchy material that can be hydrolyzed to fermentable sugars can serve as a carbon and energy source for the production of yeast. Cane and beet sugar molasses historically provided low-cost raw material for yeast fermentation. Recently, these molasses have become less attractive for yeast fermentation due to the improvement of sugar processes to recover more sucrose from molasses thereby reducing the amount of available fermentable sugars. As used herein, "sugar source" refers to the propagation and fermentation energy source for the present invention.

The present invention improves the probiotic properties of prior art (current) yeast versions in part through the use of more complex sugars during fermentation. In an aspect, the present invention utilizes a mixture of simple and complex sugars. In an aspect, the sugar source of the present invention comprises sugars with varying degrees of polymerization ("DP"). In an embodiment, the sugar source of the present invention comprises a mixture of DP1, DP2, DP3, and DP4 sugars. As it relates herein, DP1 indicates a single sugar chain, DP2 indicates two sugar chains, DP3 indicates three sugar chains, and DP4 relates to everything else. In an embodiment, the sugar source of the invention comprises from about 70 wt-% to about 80 wt-% DP1 sugar, from about 5 wt-% to about 15 wt-% DP2 sugar, from about 5 wt-% to about 15 wt-% DP3 sugar, and from about 1 wt-% to about 10 wt-% DP 4 sugar. In an embodiment, the sugar source comprises from about 74 wt-% to about 78 wt-% DP1 sugar, from about 8 wt-% to about 12 wt-% DP2 sugar, from about 8 wt-% to about 10 wt-% DP3 sugar, and from about 5 wt-% to about 6 wt-% DP4 sugar. In a preferred embodiment, the sugar source comprises about 76 wt-% DP1 sugar, about 10 wt-% DP2 sugar, about 8 wt-% to about 10 wt-% DP3 sugar, and about 5 wt-% to about 6 wt-% DP4 sugar. In a preferred embodiment, the sugar source comprises glucose (a DP1 sugar), maltose (a DP2 sugar), maltotriose (a DP3 sugar), dextrin (a DP4 sugar) and/or combinations thereof. The use of more complex sugars as an energy source produces the desired carbohydrates and amino acids which form the basis for the new yeast strains to be developed and produced by the process described herein. In an embodiment, the sugar source comprises about 3% to about 7% unfermentable salts, proteins, and/or ash. In an embodiment, the sugar source is substantially free of unfermentable salts, proteins, and/or ash.

In an aspect, the concentrations of DP1, DP2, DP3, and DP4 in the fermentation medium controls yeast growth and nutrient absorption that limits the ethanol, glycerin, and organic acid produced in the yeast fermentation process.

In an embodiment, the yeast process described herein operates as part of an existing dry mill ethanol facility to provide a reliable, low-cost sugar source. In this embodiment, a portion of the cooked corn mash from the existing ethanol production cook tank is diluted with condensate from the ethanol production and/or potable filtered water to dilute organic acids, cooled, and then saccharified with an enzyme which hydrolyzes the maltodextrins and short-chained oligosaccharides into dextrin, maltotriose, maltose, and glucose molecules, which comprises a highly compatible DP4 sugar source for the invention. In an embodiment, the enzyme is glucoamylase. The percentages of each sugar present are controlled by metered enzyme dosing and retention time. In an aspect, saccharification occurs in a saccharification tank. In an embodiment, the saccharification tank is a stainless steel tank. In an embodiment, the volume of the saccharification tank depends on the need to manage and maintain a 24-hour hold time. In an aspect, the saccharification tank comprises at least one agitator to mix the contents therein. This disclosure is meant to include any agitation system as known in the art such as a mechanical agitator, a static agitator, a rotating tank, a mixer, a paddle mixer, an impeller, a propeller, vibration, oscillation, and the like, and/or combinations thereof. In an embodiment, the agitator comprises at least one impeller, and agitation is maintained with variable speeds and variable blade pitches.

In an embodiment the converted and saccharified mash is cooled and then clarified using centrifugal separators, producing a clarified dextrin, maltotriose, maltose, and glucose sugar stream to be used as a sugar source for yeast fermentation as described herein. In an embodiment, the sugar source is stored and heated for bacteria sterilization in a container or tank before introduction into a propagator and/or fermenter. In an embodiment, the clarified sugar source comprises minerals. In an embodiment, the sugar source may be further processed to remove any minerals present.

Yeast Production as an Add-on to Existing Dry Mill Ethanol Facility

The process as disclosed herein may be used as an add-on operation to an existing dry mill ethanol production facility. The following describes a representative dry mill ethanol production facility and process.

The corn and milo feedstock for the ethanol production process is conveyed from storage and subsequently milled into a fine powder ("meal") and conveyed to a meal storage tank. The meal is metered from this storage tank to a slurry mixer where it is thoroughly mixed with process condensate and a liquifying enzyme such as alpha-amylase to produce a mash that is approximately 35 wt-% solids. The mash from the slurry mixer discharges into a cook tank wherein the corn starch in the mash is converted into sugars. Heat is applied at this stage to reduce bacteria levels in the mash and allow the enzyme to enable liquefaction where the starch is broken down into complex sugars. The mash is then cooled and pumped into ethanol fermenters for producing ethanol.

A portion of the cooked mash is diverted from the mash flow to the ethanol fermenter and into a saccharification process. Process condensate and filtered potable water is added to the mash flow to produce a thin mash that is from about 6 wt-% to about 10 wt-% total solids. This thin mash is cooled. A reducing enzyme such as gluco-amylase is added to the cooled thin mash, and the thin mash is transferred continuously into a saccharification tank wherein the reducing enzyme aids in the conversion of the sugar to dextrin, maltotriose, maltose, glucose, and/or other fermentable sugars. The saccharification tank is sized to provide adequate retention time. As used herein, "retention time" is the time required to complete conversion of the corn starch in the thin mash to sufficient varieties and amounts of fermentable sugars for maximum yeast growth in the fermentation medium. In an embodiment, the retention time is about 12 hours.

The sugar mash exiting the saccharification tank is conveyed into a horizontal decanter type (or comparable) centrifuge for separating the mash solids such as protein, fiber, and other solids, from the mash liquid stream. The solids stream exits the decanter with about 25 wt-% to about 35 wt-% solids and can be returned to the ethanol production process. The clarified dextrin, maltotriose, maltose, and glucose stream, which contains solids under about 10 microns, is pumped to a 3-phase bowl type (or comparable) centrifuge that will separate the stream into three separated parts. The first part comprises oil which is then returned to the ethanol process. The second part comprises dextrin, maltotriose, maltose, and glucose, which is then cooled and/or stored and used as the sugar source for the yeast propagation and fermentation processes as described herein. The third part comprises solids not removed in the decanter centrifuge which is collected and returned to the ethanol process.

Yeast Strain

The process described herein produces yeast strains and products that improve animal and/or human health as a natural antibiotic and medication replacement option and digestion aid when added to feed rations. Yeast cell nutrient metabolism is enhanced by varying its osmotic properties, which are primarily controlled by selective permeability of the cell wall as determined by conditions of the propagation and fermentation medium as described herein. According to the invention, yeast cell nutrient metabolization may be improved by increasing the percentage and distribution throughout the cell of complex carbohydrates.

The yeast cell wall comprises three types of polysaccharides: polymers of mannose (mannans as mannoproteins), polymers of glucose (β-glucan), and polymers of n-acetyl-glucosamine (chitin). The yeast cell wall further comprises mannan oligosaccharides ("MOS"), a known natural antibiotic replacement. Oligosaccharide is a saccharide polymer containing a small number, typically three to ten, of simple sugars or monosaccharides. Oligosaccharides have many functions including, but not limited to, cell recognition and cell binding. Generally, oligosaccharides are found either N- or O-linked to compatible amino acid side-chains in proteins or to lipid moieties.

The osmotic properties of a yeast cell are primarily controlled by selective permeability of the cell wall as determined by conditions of the propagation and/or fermentation mediums. Selective permeability controls or limits the movement of nutrients into the yeast cell. In an embodiment, the process according to the present invention controls the conditions of yeast propagation and fermentation medium environments through, for example, agitation parameters, pH monitoring and control, temperature monitoring and control, monitoring and metering nutrient levels and additions, monitoring and controlling cell size and growth cycle, management of medium dilution levels, monitoring and controlling air addition and distribution, monitoring and controlling sugar source levels, and monitoring and controlling pressure inside the propagators and fermenters. Yeast cell size, growth progress, and vibrancy are monitored with samples displayed on a grid slide viewed from a microscope. Osmotic pressure on the yeast cell wall is controlled according to the process described herein, causing rapid growth, naturally occurring enzyme secretions, and reducing the natural production of alcohol, all of which improve cell health, growth, and overall performance. In an aspect, by controlling and enhancing the osmotic properties of the yeast, yeast cell nutrient metabolism is improved by increasing the percentage and distribution throughout the cell of complex carbohydrates and increasing the absorption of nutrients improving and affecting the metabolization pathway of the yeast. This management and increase of nutrient metabolism improves the yeast cell's amino acid profile and output and increases the yeast cell's MOS level of complex carbohydrates and other beneficial complex carbohydrates while reducing the production of alcohol and organic acids such as lactic acid which can inhibit yeast performance.

In an embodiment, the yeast produced by the process disclosed herein comprises at least about 0.1 wt-%, preferably at least about 0.5 wt-%, preferably at least about 1 wt-% more MOS than prior art yeast strains. In an embodiment, the yeast produced by the process disclosed here comprises from at least about 2 wt-%, preferably at least about 5 wt-%, more preferably at least about 8 wt-% more complex carbohydrates that prior art yeast strains. In an embodiment, the yeast produced by the process disclosed here comprises at least about 0.5 wt-%, preferably at least about 2 wt-% more amino acids than prior art yeast strains.

Yeast as an Animal Feed Additive

In an embodiment, the new yeast product produced by the process described herein is used as an additive in feed for animals. In an aspect, the naturally produced amino acids and complex carbohydrates of the yeast according to the invention may be hydrolyzed by an animal's digestive tract in a gradual, steady manner and absorbed more efficiently than synthetic amino acids. MOS is a complex carbohydrate known for its ability to bind its threadlike fimbriae on pathogenic bacteria, preventing such bacteria from attaching to the animal gut wall, thus inhibiting bacteria colonization and multiplication. MOS ingestion has been demonstrated to be a viable solution for antibiotic-free diets in multiple animal species as well as furnishing effective support for digestion and immunity.

In an embodiment, an animal feed comprises from about 1 wt-% to about 10 wt-% yeast according to the invention. In an aspect, the amount of yeast added to the animal feed depends upon the type of animal and/or the development of such animal. In an embodiment, an animal feed for beef and/or dairy cattle comprises from about 1 wt-% to about 3 wt-% yeast of the invention, depending on the life cycle of the cattle. For example, during a time of calf weaning and ruminant development, an animal feed may comprise about 3 wt-% yeast according to the invention; during a time of backgrounding an animal feed may comprise about 1 wt-% yeast according to the invention; during a time of finishing an animal feed may comprise about 1 wt-% yeast according to the invention; and an animal feed for a cow calf may comprise about 2 wt-% yeast according to the invention. In an embodiment, an animal feed for swine and/or poultry may comprise from about 2 wt-% to about 4 wt-% yeast depending on amino requirements. In an embodiment, an animal feed for aquaculture may comprise from about 3 wt-% to about 5 wt-% yeast depending upon protean concentration.

In some embodiments, the animal feed may further comprise other nutrients, vitamins, and/or additives, and/or combinations thereof in addition to the yeast. As recognized in the art, an animal diet may be further supplemented with amino acids, vitamins, minerals, enzymes, organic acids, essential oils, probiotics, prebiotics, antioxidants, pigments, anti-caking agents, anti-inflammatory agents, and the like. In an embodiment, the animal feed is substantially free of additive antibiotics. In another embodiment, the animal feed may comprise additional antibiotics and/or probiotics. In an aspect, the addition of the yeast according to the invention lessens the amounts of antibiotics, probiotics, anti-inflammatory agents, vitamins, and/or minerals added to the feed.

Further disclosed herein are methods of administering to an animal a composition comprising the yeast product as described herein. The method comprises adding the yeast of the current invention to a foodstuff for animals by any manner, process, or system as known in the art, and administering the composition to an animal. Administering the combination to the animal promotes an increase in the health of the animal relative to an animal that is not administered the composition. As used herein, "administering" refers to oral administration. As used herein, "foodstuff" refers to any feed composition normally fed to an animal and includes, but is not limited to, solid and liquid animal feeds, supplements, water, and feed additive carriers. Exemplary foodstuff comprises a feed ration, a mineral supplement, a protein supplement, a premix, molasses, a liquid feed, water, or any combination thereof. In a preferred embodiment, the yeast is admixed to the foodstuff prior to administration to the animal. As used here, "animal" refers to a non-human animal. In some embodiments, the animal is a companion animal such as a pet. In other embodiments, the animal can be a domestic fowl, cow, pig, rabbit, sheep, goat, deer, bison, buffalo, alpaca, horse, donkey, llama, reptile, fish, crustacean, and the like.

The timing and duration of administration of the composition of the invention to an animal can and will vary. The composition may be administered throughout the period of feeding the animal. In an embodiment, the composition is administered at specific periods during the growth and development of the animal. In an embodiment, the feed composition may be administered during periods of heightened susceptibility of the animal to infection, or during infancy, old age, gestation, after birthing, and the like. In an embodiment, the administering of the composition comprising the yeast ameliorates at least one observed or measured deleterious symptom or sign in the animal. In other embodiments, administration delays onset of at least one observed and/or measure deleterious sign in the animal. In preferred embodiments, administration prevents onset of at least one observed and/or measured deleterious sign in the animal. Exemplary deleterious symptom or signs can include detection of a microbial infection. In an aspect, the composition can be administered daily, weekly, monthly, or multiple times during a day, or at every feeding time.

Yeast for Human Consumption

In an embodiment, the yeast product produced by the process described herein is used for human consumption, and/or as an additive in food for humans and/or as a probiotic for humans. In an embodiment, a human food product comprises the yeast product according to the invention. As used herein, a "human food product" comprises anything fit for oral consumption and may comprise food and/or beverage and/or a supplement and/or a vitamin and/or a pill and the like.

In an embodiment, the yeast product according to the invention is added to a food product and/or vitamin and/or probiotic for human consumption. In an aspect, the yeast product according to the invention is a standalone product. In an embodiment, the yeast product according to the invention is ingested by a human in a pill and/or vitamin form. In an embodiment, the yeast product according to the invention is added to a vitamin and/or pill. In an embodiment, the yeast product according to the invention is in granular and/or powder form. In an embodiment, the yeast product is added to food and/or drink by the human. In an embodiment, the yeast product according to the invention further comprises a natural flavor, an artificial flavor, a sweetener, salt, a flavor enhancer, a color additive, an emulsifier, a stabilizer, a fat, a preservative, and the like. In some aspects, the yeast product may be in the form of a liquid, a paste, a bar, a cake, a powder, a granulate, a tablet, a gum, a capsule, a lozenge, a water, a spray, a dry form, and the like.

In some embodiments, the human food product may further comprise other nutrients, vitamins, and/or additives, and/or combinations thereof in addition to the yeast. As recognized in the art, a human diet may be further supplemented with amino acids, vitamins, minerals, enzymes, organic acids, essential oils, probiotics, prebiotics, antioxidants, anti-inflammatory agents, and the like.

Further disclosed herein are methods of administering to a human a composition comprising the yeast product as described herein. The method comprises adding the yeast of the current invention to a food or drink for humans by any manner, process, or system as known in the art. In an aspect, human consumption is daily, weekly, monthly, or multiple times during a day.

What is claimed is:
1. A fermentation process that controls osmotic pressure around a yeast cell wall comprising:
providing a yeast propagation medium, a sugar source, air, and nutrients to at least one fermenter;

fermenting said yeast propagation medium creating a fermentation medium therein, wherein the fermenting produces $CO_2$, and wherein $CO_2$ and air are discharged from an air vent in a top portion of the fermenter to maintain an oxygen to $CO_2$ ratio between from about 2 to about 6 in the top portion of the fermenter during the fermentation process;

wherein the fermenter comprises at least one agitator and at least two baffles, and wherein the fermenting is under aerobic conditions.

2. The process of claim 1, wherein the sugar source comprises DP1, DP2, DP3, and DP4 sugars and is continually supplied to the fermenter during fermentation.

3. The process of claim 2, wherein the sugar source comprises from about 70 wt-% to about 80 wt-% DP1 sugar, from about 5 wt-% to about 15 wt-% DP2 sugar, from about 5 wt-% to about 15 wt-% DP3 sugar, and from about 1 wt-% to about 10 wt-% DP4 sugar.

4. The process of claim 1, wherein the fermenter comprises a cooling system and wherein the fermentation medium has a temperature between about 86° F. and about 90° F.

5. The process of claim 1, wherein pressure in the fermenter is from about 5 psi to about 10 psi.

6. The process of claim 1, wherein the fermentation medium has a pH of from about 4 to about 6.

7. The process of claim 1, wherein the sugar source comprises glucose, maltose, maltotriose, and dextrin.

8. The process of claim 1, wherein the nutrients comprise one or more of a nitrogen source, a phosphorus source, minerals, vitamins, and one or more of phosphoric acid, anhydrous ammonia, sulfuric acid, naturally occurring organic acids from the sugar source, and/or combinations thereof.

9. The process of claim 1, wherein the fermenter comprises a stainless steel tank with a has a volume of from about 50,000 gallons to about 200,000 gallons.

10. The process of claim 1, wherein the air is filtered and compressed.

11. The process of claim 1, wherein the sugar source is added to the fermenter at a rate of about 1 gallon per minute to about 80 gallons per minute.

12. The process of claim 1, wherein the fermentation medium comprises oxygen saturation levels of from about 50% to about 95% and wherein the fermentation medium comprises dissolved oxygen levels from about 8 ppm to about 25 ppm.

13. The process of claim 1, further comprising monitoring a sugar profile in the fermentation medium with high-performance liquid chromatography, monitoring complex carbohydrate and protein production, oxygen and nitrogen saturation, and/or yeast cell mass with near-infrared analysis, and monitoring yeast cell viability and budding count by grid smear examination.

14. The process of claim 1, wherein the fermenting proceeds until fermentation reaches peak growth stage.

15. The process of claim 14, wherein the fermentation takes about 6 to about 30 hours.

16. The process of claim 14, wherein the fermenter is about 75% to about 90% full at peak growth stage.

17. The process of claim 1, wherein the fermenting proceeds until the fermenter is about 75% to about 90% full.

18. The process of claim 1, wherein the fermenter is configured to adjust sugar source, air, nutrients, and pressure to maintain yeast viability and yeast budding levels.

19. The process of claim 1, wherein the process operates as a part of an existing dry mill ethanol facility.

* * * * *